United States Patent [19]
Owens

[11] Patent Number: 5,864,140
[45] Date of Patent: Jan. 26, 1999

[54] APPARATUS FOR MEASURING CHARACTERISTICS OF A LIQUID

[75] Inventor: Daniel Richard Owens, Ewenny,Mid Glamorgan, United Kingdom

[73] Assignee: Acer Consultants Limited, Surrey, United Kingdom

[21] Appl. No.: 624,543

[22] PCT Filed: Oct. 18, 1994

[86] PCT No.: PCT/GB94/02275

§ 371 Date: Jul. 1, 1996

§ 102(e) Date: Jul. 1, 1996

[87] PCT Pub. No.: WO95/11439

PCT Pub. Date:Apr. 27, 1995

[30] Foreign Application Priority Data

Oct. 18, 1993 [GB] United Kingdom ................. 93214310

[51] Int. Cl.⁶ ................................................. G01N 21/59
[52] U.S. Cl. .......................................... 250/343; 250/373
[58] Field of Search ..................... 250/343, 373, 250/356.1

[56] References Cited

U.S. PATENT DOCUMENTS

| | | | |
|---|---|---|---|
| 4,210,809 | 7/1980 | Pelavin .................................. | 250/356.1 |
| 4,462,962 | 7/1984 | Baba et al. . | |
| 4,678,278 | 7/1987 | Friesen et al. ........................... | 350/319 |
| 4,874,949 | 10/1989 | Harris et al. ............................ | 250/343 |
| 4,912,332 | 3/1990 | Siebel et al. .......................... | 250/356.1 |
| 5,010,908 | 4/1991 | McLeod et al. . | |
| 5,124,553 | 6/1992 | Hilliard et al. .......................... | 250/343 |
| 5,420,432 | 5/1995 | Manook et al. ......................... | 250/373 |

FOREIGN PATENT DOCUMENTS

| | | | |
|---|---|---|---|
| 0 171 989 | 2/1986 | European Pat. Off. . | |
| 55-62357 | 5/1980 | Japan ..................................... | 250/373 |
| 184074 | 3/1983 | New Zealand . | |
| 2 107 473 | 4/1983 | United Kingdom . | |
| 2 157 850 | 10/1985 | United Kingdom . | |
| 2 212 261 | 7/1989 | United Kingdom . | |
| 2 234 061 | 1/1991 | United Kingdom . | |
| 2 256 043 | 11/1992 | United Kingdom . | |
| WO 92/16828 | 10/1992 | WIPO . | |

*Primary Examiner*—Constantine Hannaher
*Attorney, Agent, or Firm*—Kane,Dalsimer,Sullivan,Kurucz,Levy, Eisele and Richard,LLP

[57] ABSTRACT

An apparatus for measuring characteristics of a liquid including a channel through which, during operation, the liquid flows and a plurality of sensors for measuring characteristics of the liquid as it flows through the channel. The cross-sectional shape of the channel varies along its length, but the cross-sectional area of the channel is substantially constant so that, during operation, liquid flows through the channel at a substantially uniform speed. The sensors include an ultra-violet sensor and an infra-red sensor, each having a source and a detector of electromagnetic radiation arranged along an axis transverse to the channel. The axes of the two sensors are transverse to each other.

24 Claims, 8 Drawing Sheets

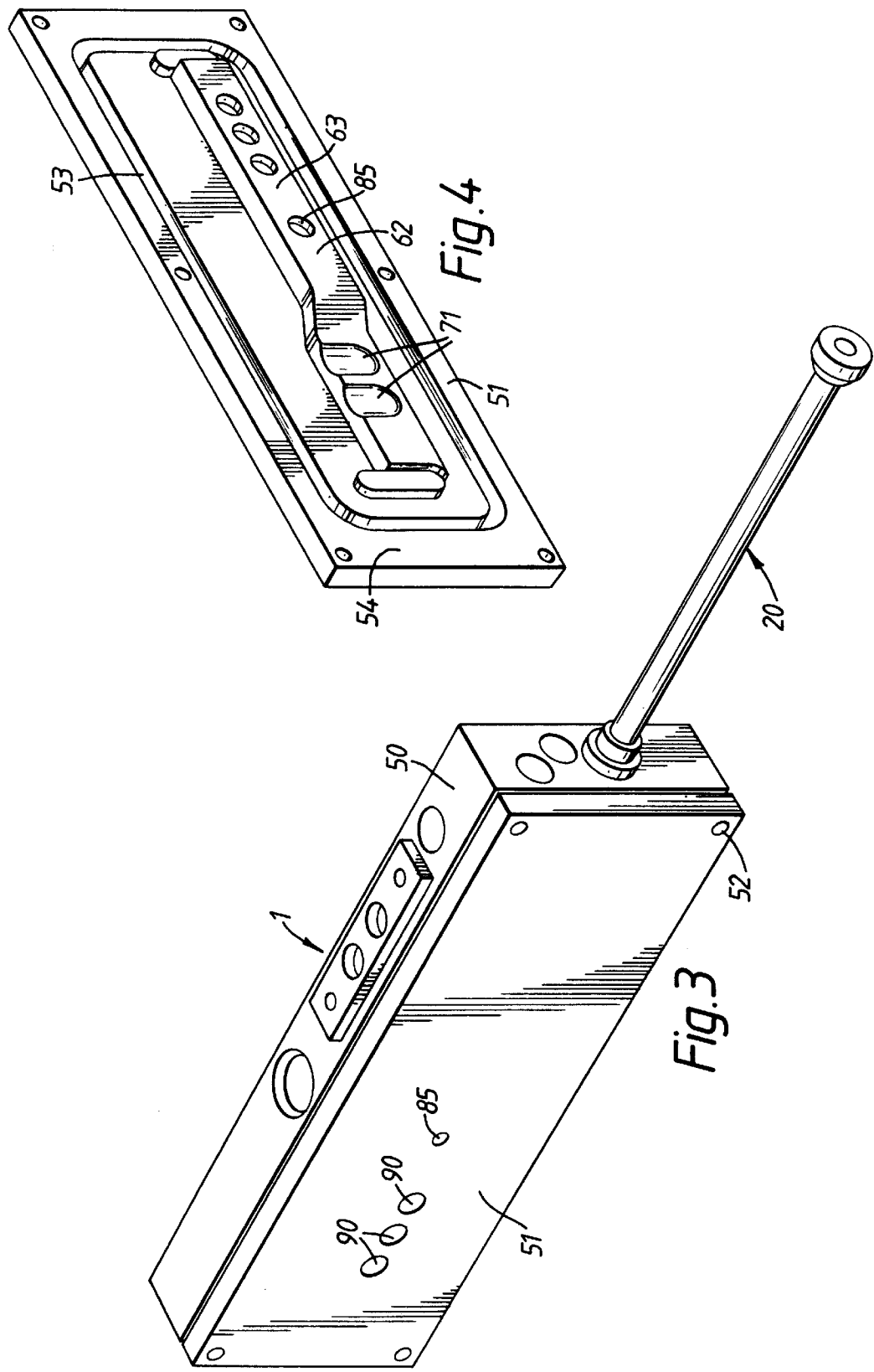

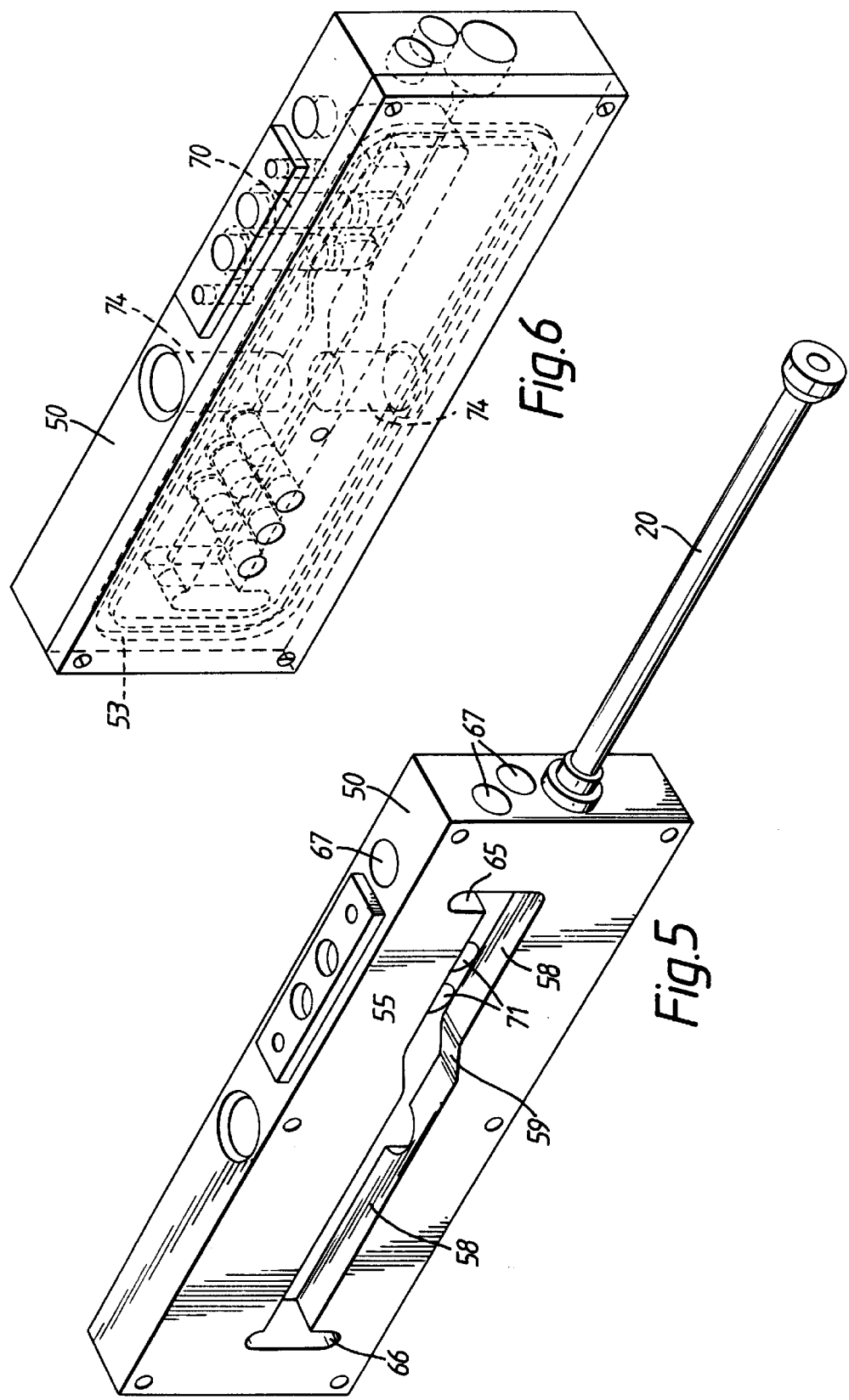

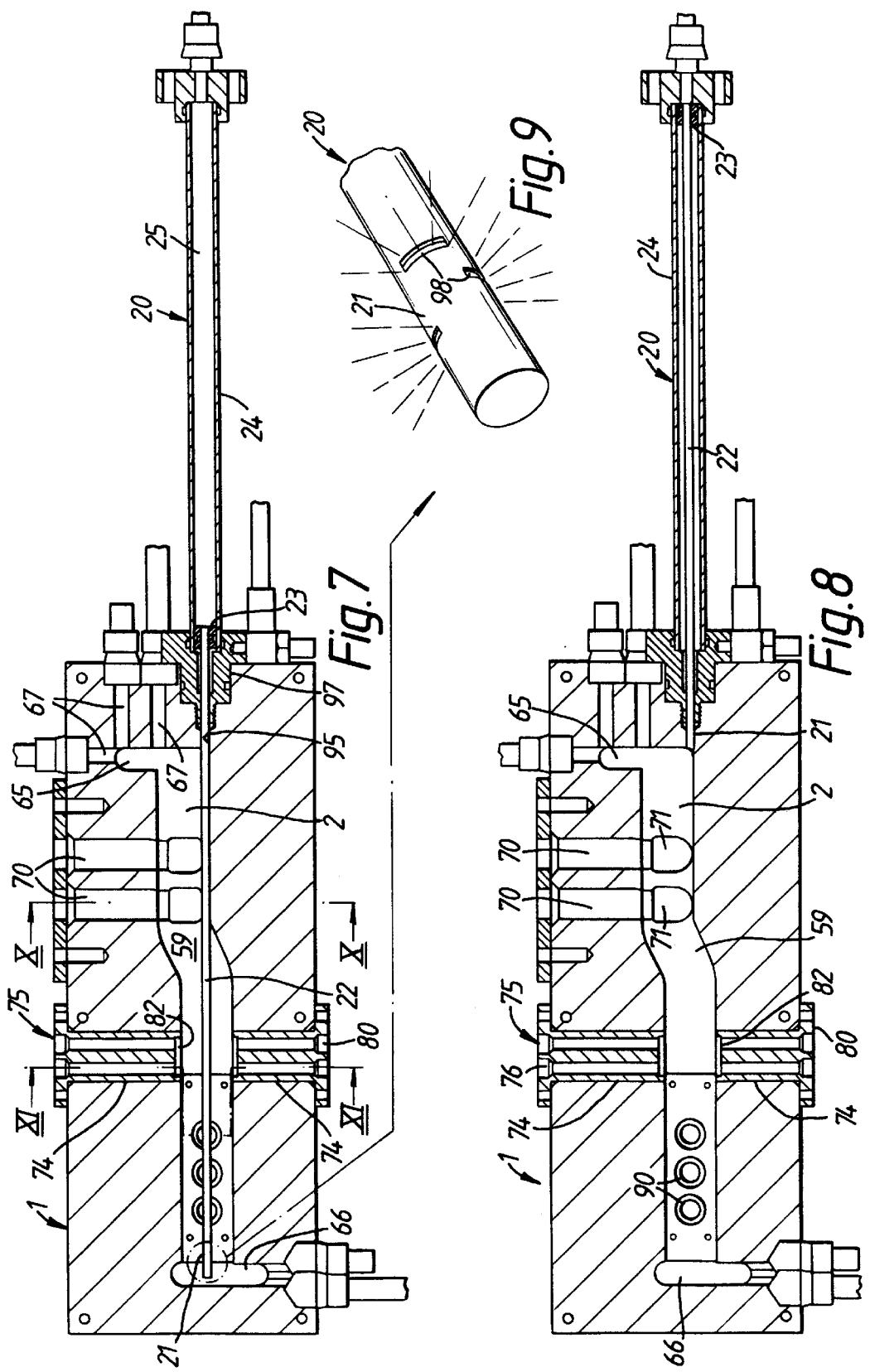

| FUNCTION | V1 | V2 | V3 | V4 | V5 | V6 | V7 | V8 | V9 | V10 | V11 | PA | PB | PC | H1 |
|---|---|---|---|---|---|---|---|---|---|---|---|---|---|---|---|
| NORMAL OP. | 0 | 0 | 0 | 0 | 0 | 0 | 0 | 0 | 0 | 0 | 0 | 1 | 0 | 0 | 0 |
| DRAIN DOWN | 0 | 0 | 0 | 0 | 0 | 0 | 0 | 0 | 0 | 0 | 0 | 0 | 0 | 0 | 0 |
| PRES. WASH | 0 | 0 | 0 | 1 | 1 | 0 | 0 | 0 | 1 | 0 | 0 | 0 | 1 | 0 | 0 |
| RAM RETURN | 0 | 0 | 1 | 1 | 1 | 0 | 0 | 0 | 0 | 0 | 1 | 0 | ■ | 0 | 0 |
| FWD. FLUSH | 1 | 0 | 1 | 0 | 0 | 0 | 0 | 0 | 0 | 0 | 0 | 0 | ■ | 0 | 0 |
| BIO. WASH | 1 | 1 | 0 | 1 | 0 | 1 | 0 | 0 | 0 | 0 | 0 | 0 | ■ | 0 | 0 |
| BIO. DRAIN | 1 | 0 | 0 | 1 | 0 | 1 | 1 | 0 | 0 | 0 | 0 | 0 | 0 | 0 | 0 |
| REV. FILTER | 1 | 0 | 0 | 0 | 0 | 0 | 0 | 0 | 0 | 0 | 0 | 0 | 1 | 0 | 0 |
| FWD.+BIO | 0 | 1 | 1 | 1 | 1 | 0 | 1 | 0 | 0 | 0 | 0 | 0 | ■ | 0 | 0 |
| HOT PRES.W | 1 | 0 | 0 | 1 | 1 | 0 | 0 | 1 | 0 | 0 | 1 | 0 | 1 | 0 | 1 |
| POT. INTAKE | 0 | 1 | 1 | 0 | 0 | 0 | 0 | 0 | 0 | 0 | 0 | 0 | ■ | 1 | 0 |
| BIO. OUT. | 0 | 0 | 1 | 0 | 0 | 0 | 0 | 0 | 0 | 0 | 0 | 0 | 0 | 0 | 0 |
| BIO. TANK CL | 1 | 0 | 1 | 1 | 0 | 0 | 0 | 0 | 0 | 1 | 0 | 0 | ■ | 0 | 0 |
| BIO. TANK DR | 0 | 1 | 1 | 1 | 0 | 0 | 0 | 0 | 0 | 0 | 0 | 0 | 1 | 0 | 0 |
| BIO. IN | 0 | 0 | 1 | 0 | 0 | 0 | 0 | 0 | 0 | 0 | 1 | 0 | # | 0 | 0 |

■ PUMP DRIVEN FORWARD AT HALF POWER.
PUMP DRIVEN IN REVERSE AT HALF POWER.

*Fig. 14*

APPARATUS FOR MEASURING CHARACTERISTICS OF A LIQUID

BACKGROUND OF THE INVENTION

1. Field of the Invention

This invention relates to an apparatus for measuring characteristics of a liquid. In particular, but not exclusively, the invention relates to an ultraviolet (UV) absorbency-based monitor for measuring the amount of organic pollution in a liquid, and is of application for on-line monitoring of water quality at locations such as industrial or water treatment plant effluent outlets, rivers or reservoirs.

2. Description of the Prior Art

A number of methods are available for determining the biological or organic pollution in water, involving the measurement of parameters such as BOD (biochemical oxygen demand), TOC (total organic carbon) or COD (chemical oxygen demand). The parameter that is usually of most interest is the BOD.

A number of on-line, continuous BOD monitors are available that operate by measuring the absorbency of ultraviolet (UV) light by a sample. These monitors are based on the principle that a particular substance will absorb light of a particular wavelength (or wavelengths), so that the reduction in intensity of light of that wavelength, when transmitted through a sample containing the substance, can be related to the concentration of that substance. Aromatic organic compounds, and other organic compounds that have conjugated double bonds, absorb light in the UV wavelength region and research has shown that absorbency measurements taken in that region, and in particular at 254 nm, can be related to BOD (and also to TOC and COD).

In one such monitor, the amount of organic matter in a liquid sample is determined by passing a liquid sample through a flow cell, passing UV and visible light through the sample and making measurements of the absorption of UV light by the sample and the absorption and scatter of visible light. The amount of organic matter in the sample is determined from the measured absorption of UV light, with the visible light measurements being used for compensation purposes.

One disadvantage of the known monitor is the tendency of the flow cell to become fouled by substances in the liquid sample, which can result in the windows for the UV and visible light monitors becoming obscured. This reduces the accuracy and efficiency of the monitor and can eventually prevent operation. It is necessary, therefore, to clean the flow cell at regular intervals, which is costly and time-consuming and can prevent automatic operation of the monitor.

OBJECTS AND SUMMARY OF THE INVENTION

There is a need, therefore, for an apparatus for measuring characteristics of a liquid, that resists fouling by substances in the liquid and which can clean itself when fouling occurs.

According to the present invention there is provided an apparatus for measuring characteristics of a liquid, the apparatus including a channel through which, during operation, the liquid flows and a plurality of sensors for measuring characteristics of the liquid as it flows through the channel, the cross-sectional area of the channel being substantially constant so that, during operation, liquid flows through the channel at a substantially uniform speed.

This reduces turbulence in the liquid, which in turn helps to reduce fouling of the channel by substances in the liquid.

Advantageously, the cross-sectional shape of the channel varies along its length, according to the requirements of the different sensors. The cross-sectional shape of the channel may vary to accommodate one or more sensors located within the channel. By varying the shape of the channel while keeping its cross-sectional area constant, the needs of the different sensors can be met, without causing turbulence in the liquid.

Advantageously, the two transverse axes of the channel are of different lengths, at least one sensor being arranged to measure a characteristic of the liquid between points at opposite ends of one of the transverse axes and at least one other sensor being arranged to measure a characteristic of the liquid between points at opposite ends of the other transverse axis.

Advantageously, at least two of the sensors are optical sensors, the optical path length through the liquid of a first of the optical sensors being longer than the optical path length through the liquid of the second optical sensor. Preferably, each optical sensor comprises a source of electromagnetic radiation located on one side of the channel and a detector of electromagnetic radiation located on the opposite side of the channel.

The sensor arrangement may be substantially the same as that described in GB 2256043A, the description of which is incorporated herein by reference.

Advantageously, the channel is shaped to produce a streamline flow of liquid through the channel.

The present invention further provides an apparatus for measuring characteristics of a liquid, the apparatus including a channel through which the liquid flows, a plurality of sensors for measuring characteristics of the liquid as it flows through the channel, and a device for washing the channel. The provision of a washing device allows the channel to be cleaned automatically to prevent excessive deposits building up in the channel.

The washing device may include a spray head that moves along the channel during operation of the washing device. The channel is advantageously-stepped, so that the spray head moves along one region of the channel in a first part thereof, and along a second region of the channel in a second part thereof. The spray head may include outlets to direct the washing liquid substantially perpendicularly to its longitudinal axis. The outlets may be arranged around substantially the entire circumference of the spray head.

The spray head may be driven hydraulically along the channel. Advantageously, the spray head is hydraulically driven by means of the washing liquid.

Advantageously, the spray head is formed on the end of a hollow rod, the rod is mounted for sliding movement along a hydraulic cylinder and the hydraulic cylinder has an inlet opening for washing liquid, the arrangement being such that when washing liquid is supplied under pressure to the hydraulic cylinder, the hollow rod is driven along the cylinder and washing liquid flows through the hollow rod to the spray head. The rod may have one or more radial slots formed its end, the slots forming the liquid outlets of the spray head.

The hydraulic cylinder may include means for returning the spray head to its starting position. The returning means may include a spring and/or means for driving the spray head hydraulically back to its starting position.

The apparatus may include means for storing a supply of washing liquid and/or means for heating the washing liquid. The apparatus may include means for supplying a chemical cleaning agent to the channel.

The apparatus may include an inlet filter, located upstream of the inlet chamber, for removing large bodies from the liquid sample.

The apparatus may include means for automatically controlling the operating sequence of the apparatus. The control means advantageously controls operation of the apparatus according to the following operating sequence:

(a) a liquid sample is pumped through the channel and its characteristics are determined by the sensors;

(b) the liquid sample is drained from the channel;

(c) the washing device is activated to wash the channel;

(d) the channel is flushed with clean water and then drained;

(e) the channel is washed with a chemical cleaning agent and then drained, and (f) the inlet filter is back-washed with clean water.

The apparatus may be for determining the amount of organic matter in a liquid. Advantageously, the apparatus includes first means for passing light of a wavelength in the UV region through the liquid sample and sensing the emergent UV light intensity, second means for making a measurement to provide an indication of the absorption by the sample of light, and third means for making a further measurement to provide an indication of the amount of scatter of light caused by the sample.

The apparatus may include processing means for determining the amount of organic matter in the sample from an output of the first means, adjusted in accordance with outputs from the second and third means.

The present invention yet further provides, a method of cleaning a channel which is in an apparatus for measuring characteristics of a liquid and through which the liquid flows, the method comprising the steps of draining the liquid from the channel and moving a washing device having a spray head along the channel whilst spraying the channel with washing liquid.

Advantageously, the method further comprises the step of flushing the channel with washing liquid.

Advantageously, the method further comprises the step of flushing the channel with a chemical cleaning agent, for example a biocide or a detergent.

The method may further comprise the step of back-washing an inlet filter with washing liquid.

Advantageously, the operating sequence of the steps is controlled automatically.

BRIEF DESCRIPTION OF THE DRAWINGS

By way of example, an embodiment of the invention will now be described with reference to the accompanying drawings, in which:

FIG. 3 is a perspective view of the flow cell and the washing device;

FIG. 4 is a perspective view front cover of the flow cell;

FIG. 5 is a perspective view of the flow cell with the front cover removed;

FIG. 6 is a perspective view of the assembled flow cell, showing internal structural details;

FIGS. 7 and 8 are side views of the flow cell and the washing device in cross section;

FIG. 9 is a perspective view of the spray head of the washing device;

FIG. 14 is a logic diagram, showing the operating sequence for the valves and pumps of the apparatus.

DETAILED DESCRIPTION OF THE PREFERRED EMBODIMENT

The monitor, which is capable of being used for on-line, continuous monitoring of liquid quality in a variety of on-site locations, comprises a single, weatherproof unit having separate compartments containing the hydraulic system and the electronic measurement and control circuits of the monitor.

Figure 1:
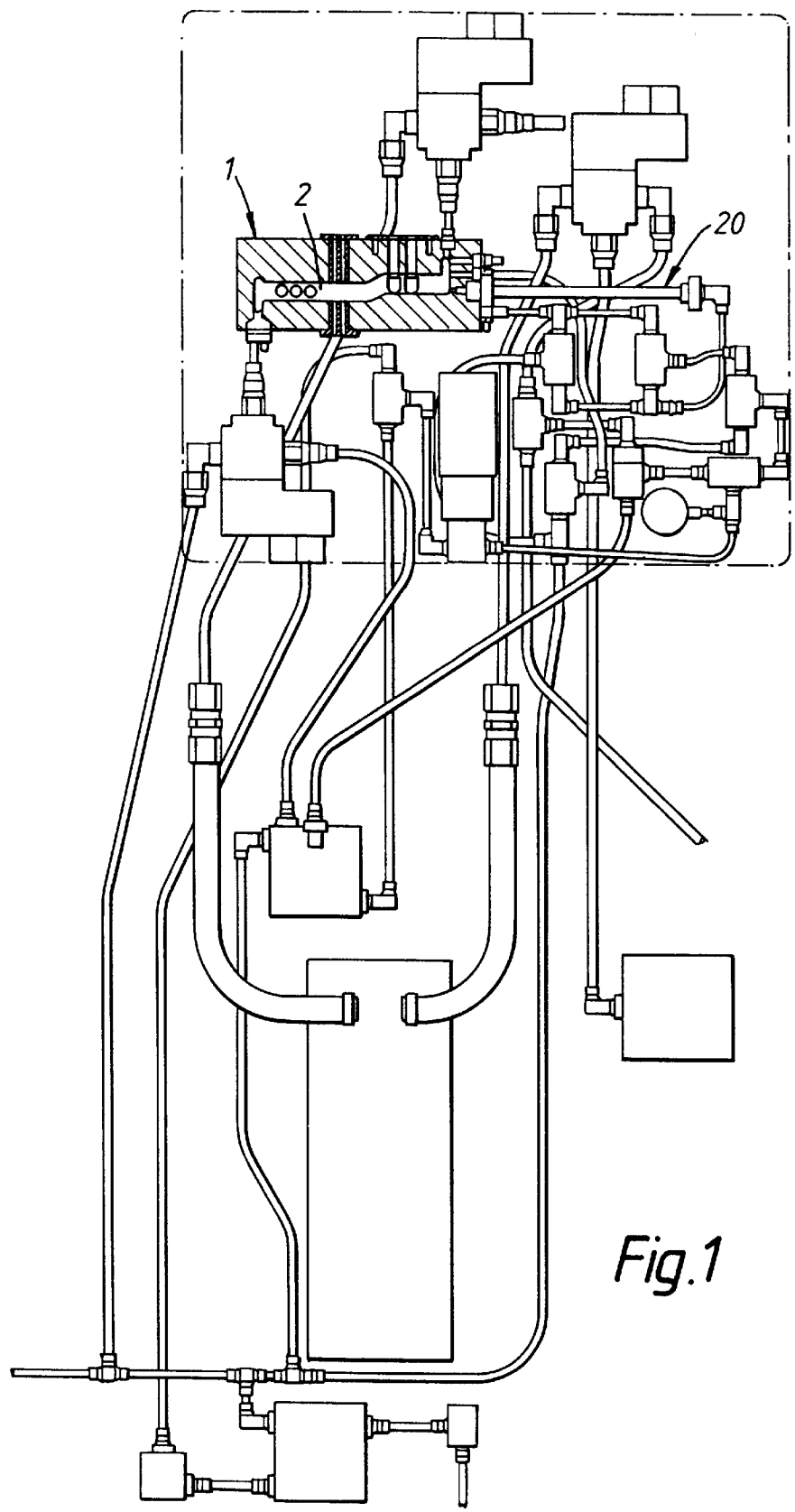
FIG. 1 is a front view of the hydraulic system of the apparatus.
Figure 2:
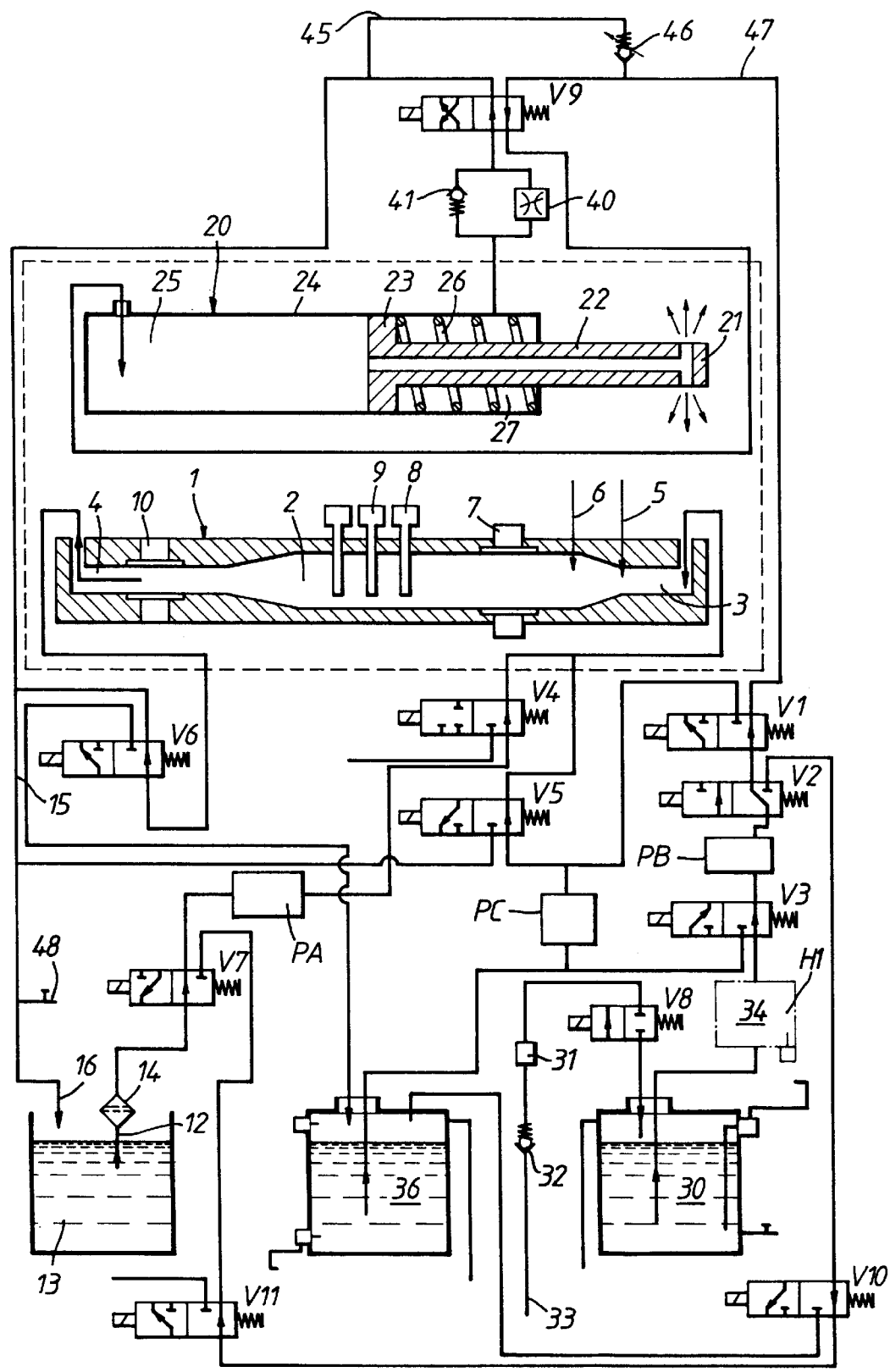
FIG. 2 is a diagrammatic representation of the hydraulic system.

The hydraulic system is shown schematically in FIG. 2 and includes a flow cell 1 having a fluid flow channel 2 with an inlet opening 3 at one end and an outlet opening 4 at the other end. The flow cell 1 includes a number of sensors for measuring characteristics of the liquid flowing through the channel. Those sensors include a pressure switch 5, a temperature probe 6, an optical sensor 7 comprising one or more infrared or visible light LEDs, probes 8,9 for measuring the pH and conductivity of the liquid sample and a UV sensor 10, which may operate at one or more UV wavelengths.

A sampling device 12 for drawing a liquid sample from a sample ditch 13 is connected via a filter 14 and a valve V7 to a pump PA, and from there via valve V4 to the inlet opening 3 of the channel 2. The outlet opening 4 of the channel 2 is connected via valve V6 and a drain line 15 to an outlet 16, for returning the sample to the sample ditch 13.

The hydraulic system includes a jet washing device 20 for cleaning the channel 2 in the flow cell 1. The jet washing device 20, which is coaxially arranged with respect to the flow cell 1 (as shown in FIG. 7), includes a spray head 21 mounted on the end of a hollow rod 22. The hollow rod 22 includes a piston 23 at its other end and is mounted for sliding movement in a hydraulic cylinder 24. The bore of the hollow rod 22 connects the spray head 21 to the primary chamber 25 of the cylinder 24. A return spring 26 is provided in the secondary chamber 27 of the cylinder 24, between the piston 23 and the end wall of the cylinder.

The primary chamber 25 of the cylinder 24 is connected via valves V9, V1, V2, V3 and pump PB to a tank 30 of potable water, which is filled via valve V8, input filter 31 and one-way valve 32 from a supply 33. Water may be pumped by pump PB from the tank 30 into the primary chamber 25, forcing the piston 23 along the cylinder 24 against the resistance of the return spring 26. This causes the spray head 21 to move along the flow channel 2 of the flow cell 1. At the same time, water flows from the primary chamber along the bore in the hollow rod 22 to the spray head 21, where it emerges to provide a number of powerful jets for cleaning the channel 2 of the flow cell 1. The water may be heated by a heater H1 in a tank 34, located downstream of the tank 30. If desired, liquids other than potable water may be used for cleaning the channel 2. For example, raw water or effluent may be used.

By activating valve V3, a chemical cleaning agent, for example a detergent or a concentrated biocide, may be pumped from a tank 36 into the cylinder 24 to provide a jet wash. Valve V6 is also then activated, to return the cleaning agent from the outlet opening 4 of the channel 2 to the tank 36.

Outward movement of the piston 23 is damped by water in the secondary chamber 27 of the cylinder, which escapes as the piston advances through an adjustable needle valve 40 and via valve V9 to the sample ditch 13. By activating valve V9, water may be pumped into the secondary chamber of the cylinder through a one-way valve 41, to drive the piston 23 back to its starting position. Water in the primary chamber 25 escapes as the piston 23 returns via valve V9 and the outlet 16 to the sample ditch 13.

Activating valve V1 allows potable water (heated if necessary) to be pumped via valve V5 directly into the into inlet opening 3 of the channel 2. A chemical cleaning agent may be added to the water by activating a metering pump PC.

The filter 14 may be back-washed by activating valves V2 and V7 and pump PB, causing potable water to flow through valves V10 and V11 to the sample ditch 13.

Activating valve V10 allows-water to be pumped into the tank 36, to wash the tank. Activating valve V11 and pump PB allows water to be drained from the water tank 30. A line 45 containing an adjustable pressure relief valve 46 connects water supply line 47 on the upstream side of valve V9 to the drain line 15, to allow water to flow to the sample ditch 13 if the water pressure exceeds a predetermined value. A sample tap 48 is provided in the drain line 15 upstream of the outlet 16, to allow a sample of liquid leaving the flow cell 1 to be drawn for testing purposes.

The flow cell 1 and the jet wash device are shown in more detail in FIGS. 3 to 8. The flow cell 1 comprises a main housing 50 and a front cover 51 that are joined to one another in a face-to-face relationship by bolts 52. A groove 53 extends around the periphery of the engagement face 54 of the front cover 51, and receives an O-ring. When the front cover 51 and the main housing 50 are bolted together, the O-ring is compressed between the engagement faces 54,55 of the front cover 51 and the main housing 50, to form a water-tight seal.

A groove 58 of elongate rectangular cross section is formed in the engagement face 55 of the main housing 50. The three faces of the groove 58 form the top, bottom and one side wall of the fluid flow channel 2. The groove 58 includes a step 59 of approximately half its height, approximately half way along the groove.

The front cover 51 includes a similarly-shaped raised formation 62 on its engagement face 55, which fits into the groove 58 when the main housing 50 and the front cover 51 are joined to one another. The upper surface 63 of the formation 62 forms the other side wall of the channel 2.

Enlarged portions at either end of the groove 58 form the inlet and outlet chambers 65,66 for the liquid sample. Fluid flow channels 67 having fittings for fluid supply lines at their outer ends extend from the top, bottom and end faces of the main housing to the inlet and outlet chambers 65,66.

Figure 10:
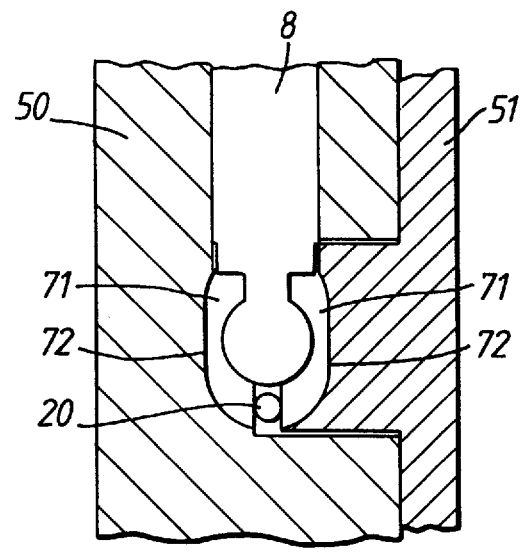
FIG. 10 is a cross-section through the flow cell on line X—X.

Two cylindrical bores 70 extend downwards from the top face of the main housing 50 to intersect the groove 58 between the inlet chamber 65 and the step 59. The bores 70 provide insertion channels for the conductivity and pH probes 9,8 (which may also include a temperature sensor). Recesses 71 are provided in the two side walls 72 of the channel 2 adjacent the conductivity and pH probes 9,8, widening the channel at those points (as can be clearly seen in FIGS. 4, 5 and 10). The recesses 71 are shaped such that the cross-sectional area of the channel 2, with the probes 9,8 inserted, remains constant throughout its length. This ensures that liquid flows through the channel 2 at a constant speed, which reduces turbulence and minimizes fouling of the channel.

Figure 11:
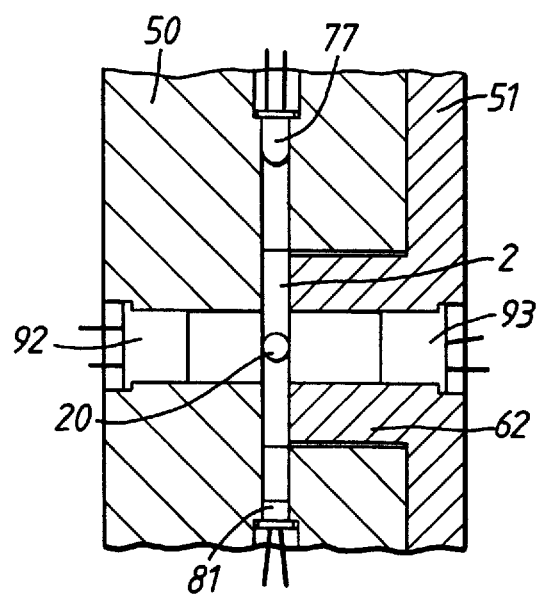
FIG. 11 is a cross-section through the flow cell on line XI—XI.

Downstream of the bores 70 for the insertion probes 9,8, between the step 59 and the outlet chamber 66, two further bores 74 extend vertically from the top and bottom faces of the main housing 50, to intersect the top and bottom walls of the channel 2 at opposite points. The bores 74 house an infrared (IR) monitor 75, for assessing the scattering and absorption by the liquid sample. The monitor 75 comprises an IR light source 76 comprising one or two light emitting diodes (LEDs) 77 and a detector unit 80, including one or two corresponding silicon photodiodes 81. Windows 82 are provided at the inner ends of the light source 76 and the detector unit 80. As shown in FIG. 11, the source 76 and the detector unit 80 are located at opposite ends of the longer axis of the elongate rectangular cross section channel 2, so that the path length of the IR light through the liquid sample is long.

A horizontal bore 85 having a window 86 at its inner end extends through the front cover 51 to intersect the light path of the IR light as it passes through the channel 2. The bore 85 houses a further photodiode 87, which measures the amount of light scattered by the sample.

Further downstream, three further sets of bores 90 extend horizontally through the main housing 50 and the front cover 51 to intersect the side walls 72 of the channel. Windows 91 are provided at the inner ends of the bores. The bores 90 house an ultraviolet (UV) monitor 10, comprising a source 92 of UV and visible light located adjacent the bores on one side of the flow cell 1 and three detector 93 located in the opposite bores. As illustrated in FIG. 11, the source 92 and the detectors 92,93 are positioned at opposite ends of the shorter axis of the elongate rectangular cross-section of the channel 2, so that the path length of light through the liquid sample is short. The three monitors 10 operate at different wavelengths, for example at ultraviolet wavelengths 254 nm and 313 nm and the visible wavelength 405 nm. The visible band at 405 nm is used for determining the color of the sample.

A further bore 95 extends from the inlet chamber 65 parallel to the longitudinal axis of the flow cell 1 to the adjacent end face 96 of the main housing 50. A fitting 97 for the jet wash device 20 is provided at the outer end of the bore. The bore 95 is positioned at the lower end of the inlet chamber 65 so that, when the jet wash probe extends into the channel 2, as shown in FIGS. 7, 8, 10 and 11, the spray head 21 moves along the bottom of the channel upstream of the step 59, so that it passes underneath the conductivity and pH probes 9,8 and along the center of the channel 2 downstream of the step 59, so that it cleans the UV detector windows 91 effectively.

As shown in FIG. 9, the spray head 21 is formed by cutting four radial slots 98 in the cylindrical wall of the hollow rod 22 and closing the end of the rod. The slots 98 are equiangularly displaced around the circumference of the rod 22 and each extends over an arc of at least 90°, so that the spray head 21 provides a full 360° jet wash.

Figure 12:
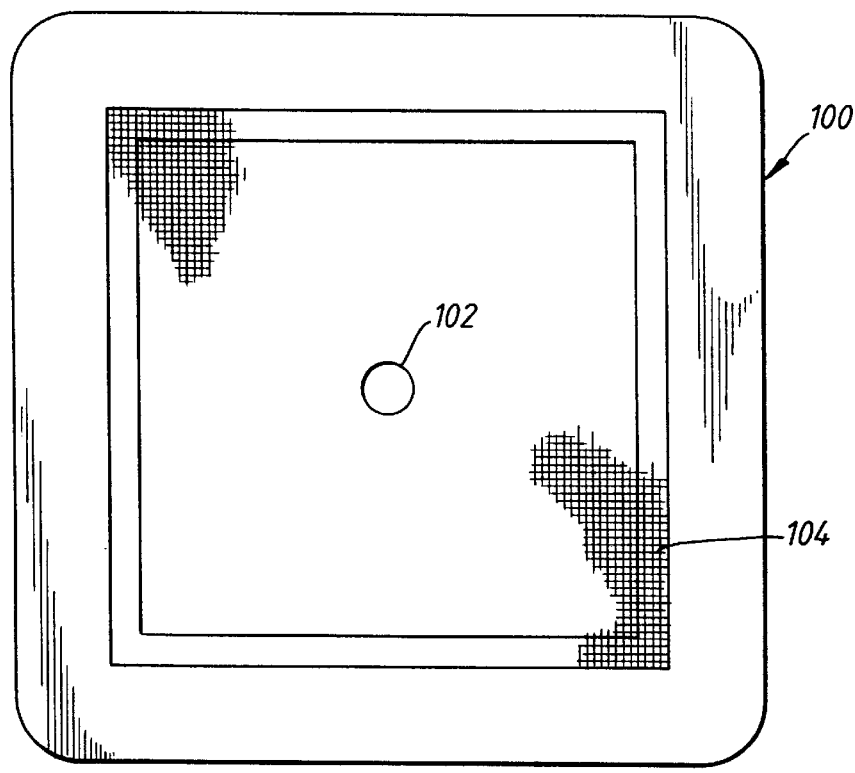
FIG. 12 is a bottom view of the inlet device.
Figure 13:
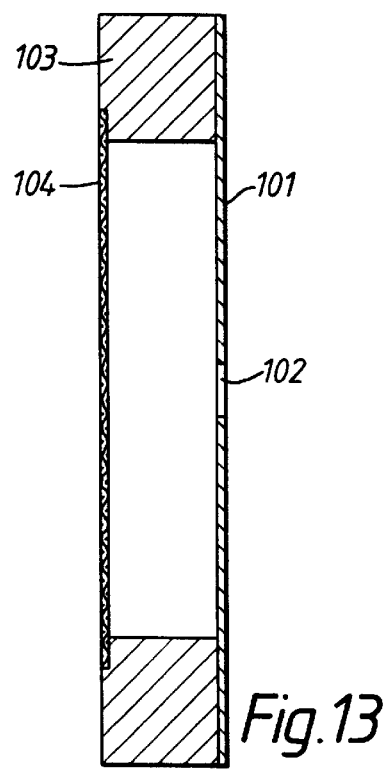
FIG. 13 is a side view in cross-section of the inlet device.

The sampling device 100 is shown in more detail in FIGS. 12 and 13. The sampling device 100 includes a square top plate 101 having a central aperture 102 to which an inlet line is connected. A square float 103 having a hollow center is attached to the lower surface of the top plate 101 and a filter mesh 104 extends across the opening in its lower face. When the sampling device is placed in the sample ditch, it floats with the filter mesh 104 just beneath the surface of the liquid, to prevent the mesh becoming obstructed by floating matter. When pump PA is activated, a sample is drawn into the inlet line through the filter mesh 104.

The usual operating sequence of the monitor is as described below, the valves and pumps activated in each step of the operating sequence being represented diagrammatically in FIG. 14. The operating sequence is normally carried out automatically under the control of a microprocessor.

During normal operation of the monitor, all the valves are deactivated and only pump PA is activated to draw a sample of liquid from the sample ditch and pump it at a steady rate through the flow cell 1 for testing. The smooth shape of the channel in the cell and its uniform cross sectional area ensure that the flow of liquid through the channel is substantially streamline (i.e. without turbulence), which helps to prevent fouling of the cell.

Eventually, however, the cell will need to be cleaned, and the first step in the cleaning operation is to allow the sample liquid to drain from the flow cell 1 by deactivating the pump PA. Valves V4 and V5 and pump PB are then activated to wash the channel with potable water, using the jet wash device 20. When the spray head reaches the end of the channel 2, valve V9 is activated and pump PB is driven at half power to return the spray head to its starting position.

The channel is then flushed with water by activating valves V1 and V11 and operating pump PB at half power, after which it is drained.

The next step is a wash with a chemical cleaning agent, which is achieved by activating valves V1, V3, V4 and V8 and operating pump PB at half power. The cleaning agent is then allowed to drain from the channel to the tank 36 by deactivating the pump PB.

Finally, the filter 14 is back washed with water by operating valves V2 and V7 and the pump PB.

Other operating steps, which may form part of the operating sequence or may be for maintenance of the monitor, include flushing the channel 2 with a mixture of water and cleaning agent, providing a jet wash with hot water, filling the water tank with water, emptying the cleaning agent tank to a service container, draining the cleaning agent tank to the sample ditch and filling the tank from a service container. The valves and pumps activated for each of those steps is represented diagrammatically in FIG. 14.

Although the invention has been described primarily in terms of an organic pollutant monitor, it may also be used for other applications.

What is claimed is:

1. An apparatus for measuring characteristics of a liquid, the apparatus including a channel through which, during operation, the liquid flows and a plurality of sensors for measuring characteristics of the liquid as it flows through the channel, the internal cross-sectional shape of the channel varying to accommodate a plurality of sensors located within the channel for measuring respective characteristics of the liquid, the internal cross-sectional area of the channel being substantially constant so that, during operation, liquid flows through the channel at a substantially uniform speed, the sensors including a first optical sensor which comprises a source of electromagnetic radiation and a detector of electromagnetic radiation and which is arranged along a first axis transverse to the channel and a second optical sensor which comprises a source of electromagnetic radiation and a detector of electromagnetic radiation and which is arranged along a second axis transverse to the channel and transverse to the first axis, the optical path length through the liquid of the first optical sensor being longer than the optical path length through the liquid of the second optical sensor.

2. An apparatus according to claim 1, in which the wavelength of the electromagnetic radiation detected by the detector of the first sensor is in the infra-red region and the wavelength of the electromagnetic radiation detected by the-detector of the second sensor is in the ultra-violet region.

3. An apparatus according to claim 1, in which the channel is shaped to produce a streamline flow of liquid through the channel.

4. An apparatus according to claim 1 including a device for washing the channel.

5. An apparatus according to claim 4, in which the washing device includes a spray head that moves along the channel during operation of the washing device.

6. An apparatus according to claim 5, in which the channel is stepped, so that the spray head moves along one region of the channel in a first part thereof, and along a second region of the channel in a second part thereof.

7. An apparatus according to claim 5, in which the apparatus includes a supply of washing liquid and the spray head includes outlets to direct the washing liquid substantially perpendicularly to its longitudinal axis.

8. An apparatus according to claim 7, in which the outlets are arranged around substantially the entire circumference of the spray head.

9. An apparatus according to claim 5, in which the spray head is driven hydraulically along the channel.

10. An apparatus according to claim 9, in which the apparatus includes a supply of washing liquid and the spray head is hydraulically driven by means of the washing liquid.

11. An apparatus according to claim 5, in which the spray head is formed on the end of a hollow rod, the rod is mounted for sliding movement along a hydraulic cylinder and the hydraulic cylinder has an inlet opening for washing liquid, the arrangement being such that when washing liquid is supplied under pressure to the hydraulic cylinder, the hollow rod is driven along the cylinder and washing liquid flows through the hollow rod to the spray head.

12. An apparatus according to claim 11, in which the rod has one or more radial slots formed at its end, the slots forming the liquid outlets of the spray head.

13. An apparatus according to claim 11, in which the hydraulic cylinder includes means for returning the spray head to its starting position.

14. An apparatus according to claim 13, in which the returning means includes a spring.

15. An apparatus according to claim 13, in which the returning means includes means for driving the spray head hydraulically back to its starting position.

16. An apparatus according to claim 4, including means for storing a supply of washing liquid.

17. An apparatus according to claim 4, including a supply of washing liquid and means for heating the washing liquid.

18. An apparatus according to claim 4, including means for supplying a chemical cleaning agent to the channel.

19. An apparatus according to claim 4, including an inlet chamber upstream of the channel and an inlet filter, located upstream of the inlet chamber, for removing large bodies from the liquid.

20. An apparatus according to claim 19, in which a control means controls the operation of the apparatus according to the following operating sequence:

(a) a liquid sample is pumped through the channel and its characteristics are determined by the sensors;

(b) the liquid sample is drained from the channel;

(c) the washing device is activated to wash the channel;

(d) the channel is flushed with clean water and then drained;

(e) the channel is washed with a chemical cleaning agent and then drained, and (f) the inlet filter is back-washed with clean water.

21. An apparatus according to claim 4, including means for automatically controlling the operating sequence of the apparatus.

22. An apparatus according to claim 1, for determining the amount of organic matter in a liquid.

23. An apparatus according to claim 22, the apparatus being so arranged that, during operation, (a) light of a first wavelength, in the UV region, is passed through the liquid sample so that a first measurement may be made that provides an indication of the emergent UV light intensity, (b) light of a second wavelength, different from the first wavelength, is passed through the liquid sample so that a second measurement may be made that provides an indication of the absorption by the liquid sample of light of that second wavelength, and (c) a third measurement may be made that provides an indication of scatter of light caused by the liquid sample.

24. An apparatus according to claim 23, including processing means for determining the amount of organic matter in the liquid sample from an output representative of the first measurement, adjusted in accordance with outputs representative of the second and third measurements.

* * * * *